US005723636A

United States Patent [19]
Fenelli et al.

[11] Patent Number: 5,723,636
[45] Date of Patent: Mar. 3, 1998

[54] METHYLTRIOXORHENIUM-UREA HYDROGEN PEROXIDE EPOXIDATION OF OLEFINS

[75] Inventors: Steven P. Fenelli, Hillsborough; Rose Ann Schultz, Princeton, both of N.J.

[73] Assignee: National Starch and Chemical Investment Holding Corporation, Wilmington, Del.

[21] Appl. No.: 631,388

[22] Filed: Apr. 12, 1996

[51] Int. Cl.$^6$ .................................................. C07D 301/19
[52] U.S. Cl. ............................................ 549/529; 502/152
[58] Field of Search .............................. 549/529; 502/152

[56] References Cited

U.S. PATENT DOCUMENTS

| | | | |
|---|---|---|---|
| 5,155,247 | 10/1992 | Herrmann et al. | 556/46 |
| 5,166,372 | 11/1992 | Crocco et al. | 549/531 |

OTHER PUBLICATIONS

Herrmann W. A., et al., "Methyltrioxorhenium as a Catalyst for Olefin Oxidation", Angew. Chem. Int. Ed. Engl., 30(12), pp. 1638–1641, 1991.

Gonsalves, et al., "Metal–assisted Reactions. Part 21. Epoxidation of Alkenes Catalysed by Manganese–prophyrins: The Effects of Various Oxidatively–stable Ligands and Bases", J. Chem. Soc. Perkin Trans. 1, pp. 546–649, 1991.

Adam, Waldemar and Mitchell Caterine M., "Methyltrioxorhenium (VII)–Catalyzed Epoxidation of Alkenes with the Urea/Hydrogen Peroxide Adduct", Amgew. Chem. Int. Ed. Engl. 1996, 35, No. 5, pp. 533–534.

"Epoxidation of Allyl and Homoallyl Trimethylsilyl Ethers with t–Butyldioxytrimethylsilane and Silicon Lewis Acid/Vanadium Catalyst", Tamejiro Hiyama, et al., Tetrahedron Letters, vol. 24, No. 4, pp. 395–398, 1983.

"Enantioselective Epoxidation of Chromene Derivatives Using Hydrogen Peroxide as a Terminal Oxidant", Ryo Irie, et al., Synlett, (1994), pp. 255–256.

"Dissociation of Hydrogen Peroxide Adducts in Solution: The Use of Such Adducts for Epoxidation of Alkenes", Antonio M. d'A. Rocha Gonsalves, et al., J. Chem. Research (S), (1991) pp. 208–209.

"A Very Simple Oxidation of Olefins and Ketones with UHP–Maleic Anhydride", Luis Astudillo, et al., Heterocycles, vol. 36, No. 5, 1993, pp. 1075–1080.

*Primary Examiner*—C. Warren Ivy
*Assistant Examiner*—Lyman H. Smith
*Attorney, Agent, or Firm*—Jane E. Gennaro

[57] ABSTRACT

A process for the epoxidation of olefins comprises contacting the olefin with urea-hydrogen peroxide in the presence of a rhenium oxide catalyst in an organic solvent.

3 Claims, No Drawings

METHYLTRIOXORHENIUM-UREA HYDROGEN PEROXIDE EPOXIDATION OF OLEFINS

FIELD OF THE INVENTION

The present invention relates to the epoxidation of olefins with rhenium (VII) complexes.

BACKGROUND OF THE INVENTION

The epoxidation of olefins utilizing hydrogen peroxide as the oxidant is a widely practiced method to make epoxy compounds. In recent years, rhenium complexes have been reported as effective catalysts with hydrogen peroxide. However, this procedure has been shown to require anhydrous hydrogen peroxide. Hydrogen peroxide is commercially available only in the form of aqueous solutions, and aqueous conditions tend to favor further reaction of the epoxide to give the diol. Thus, the procedures in the open literature in which rhenium (VII) is used take steps to dry the hydrogen peroxide solution in an alcohol prior to its use.

For example, U.S. Pat. No. 5,155,247 issued on Oct. 13, 1992, teaches the epoxidation of olefins using rhenium (VII) complexes in conjunction with hydrogen peroxide under near anhydrous conditions. The water in the hydrogen peroxide solution is removed by diluting the aqueous solution with tert-butyl alcohol, drying the solution over anhydrous magnesium sulfate, and removing the hydrated salt by filtration. The rhenium complex is then added to the alcoholic hydrogen peroxide solution followed by the addition of the olefin to carry out the epoxidation. The reaction must be conducted at relatively low temperatures, for example, −30° C. to +10° C., so that the oxidation leads selectively to the epoxide and further reaction to form the diol is suppressed. The required steps to provide the anhydrous conditions and the requirement of low temperatures under which the reaction is carried out make this procedure impractical on a commercial scale.

U.S. Pat. No. 5,166,372 issued on Nov. 24, 1992, describes the use of nitrogen containing heterocycles as ligands to rhenium catalysts used with hydrogen peroxide to epoxidize olefins. The reference claims that this class of organorhenium oxide catalysts tends to produce the lowest levels of undesired 1,2-diol side-products formed by hydrolysis. However, these compounds also modulate the activity of the catalysts downward, and thus slow the reaction rate considerably. The disclosed epoxidation method further employs a secondary alkyl aryl alcohol in combination with molecular oxygen to produce the hydrogen peroxide in situ. One of the byproducts of this reaction is the corresponding alkyl aryl ketone, which must then be hydrogenated over a platinum or palladium catalyst to convert it back to the alkyl aryl alcohol. In addition, the water content of the reaction mixture is sought to be maintained below four weight percent, and most preferably below one weight percent, by removing water formed during the oxidation from the reaction vessel with unreacted oxygen and inert gases. As can be understood, this technology requires specialized equipment that makes the method commercially unattractive.

The invention disclosed herein provides not only solutions to these problems, but also substantial improvements in the yields of epoxides from olefins such as allyl benzenes and allyl ethers, which are notoriously difficult to epoxidize.

SUMMARY OF THE INVENTION

This invention is a process for epoxidizing olefins that does not require the drying of hydrogen peroxide, or the use of catalysts with nitrogen containing ligands, or specialized equipment and conditions to reduce or eliminate the formation of undesired glycols.

The process comprises reacting the olefin with urea-hydrogen peroxide in an organic solvent in the presence of an organorhenium VII oxide catalyst under ambient conditions of temperature and pressure.

The utilization of crystalline urea-hydrogen peroxide as the source of hydrogen peroxide for epoxidation of olefins provides anhydrous peroxide without the need for specialized apparatus or drying procedures and effectively suppresses diol formation. Moreover, the stoichiometry of the 1:1 addition complex of the urea-hydrogen peroxide is fixed, thereby obviating the need to titrate to determine the peroxide concentration. In addition to these advantages, it has also been found that both improved conversions and faster reaction rates are obtained when urea-hydrogen peroxide is employed as the oxidant.

DETAILED DESCRIPTION OF THE INVENTION

The preparation of the requisite rhenium complex can be accomplished by the synthetic route illustrated by equation (1):

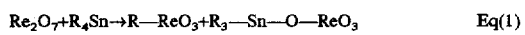

$$Re_2O_7 + R_4Sn \rightarrow R—ReO_3 + R_3—Sn—O—ReO_3 \quad \text{Eq(1)}$$

An additional improvement in the chemistry outlined in equation (1) is obtained on adding a perfluorinated anhydride prior to the tetraalkyltin compound, which allows for conversion of the trialkylstanyl perrhenate into the desired alkyltrioxorhenium complex, as outlined in equation (2):

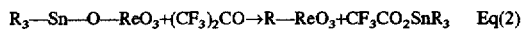

$$R_3—Sn—O—ReO_3 + (CF_3)_2CO \rightarrow R—ReO_3 + CF_3CO_2SnR_3 \quad \text{Eq(2)}$$

Any organorhenium oxide compound that is active as an epoxide catalyst for the hydrogen peroxide oxidation of an olefin may be employed in the process of this invention. The most commonly used rhenium complex is that in which R=CH$_3$, methyltrioxorhenium (hereinafter MTO), which is stable under ambient conditions. A detailed synthetic method for methyltrioxorhenium is given in U.S. Pat. No. 5,155,247 at column 8. Briefly, the procedure and exemplary reagent amounts are as follows:

All solvents must be thoroughly dried before use. The reaction vessel is dried at 400°–600° C. under high vacuum before weighing in the starting material, 10.00 g, (20.64 mmol) of dirhenium heptoxide, Re$_2$O$_7$. Tetrahydrofuran, 90 ml, is added with vigorous stirring to dissolve the Re$_2$O$_7$, followed by the addition of commercially available tetramethylstannane, Sn(CH$_3$)$_4$, 3.15 ml (22.71 mmol). This reagent is toxic and all operations must be carried out with suitable precautions. The reaction mixture is then heated at reflux for four hours. The solution is cooled to room temperature and the solvent slowly removed under reduced pressure until the residue has a paste-like consistency. At this point the reaction apparatus is provided with a cold finger condenser cooled to between −10° C. and 0° C. to prevent excessive sublimation of the target rhenium complex. After the solvent is completely removed, the product is isolated in the form of colorless needles at about 80° C. by sublimation under vacuum.

Alternatively, the methyltrioxorhenium complex can be obtained commercially from Aldrich Chemical, catalogue #41,291-0.

The urea-hydrogen peroxide is a crystalline compound and can be obtained from commercial sources.

The epoxidation preferably is carried out by the addition of the olefin to a solution of urea-hydrogen peroxide in tert-butyl alcohol that also contains the dissolved rhenium (VII) complex. The reaction is conducted at ambient temperature and pressure and does not require specialized or dedicated reactors. The amount of catalyst is not critical, but should be sufficient to accomplish the desired epoxidation reaction in a short period of time. The optimum quantity is found to depend upon a number of factors, including reaction temperature, olefin reactivity and concentration, and hydrogen peroxide concentration. The amount of urea-hydrogen peroxide relative to the amount of olefin is not critical, provided that at least one equivalent of hydrogen peroxide is present per equivalent of a mono-unsaturated olefin. It is, however, preferable to use an excess of the peroxide to optimize the yield of epoxide; nevertheless, as will be understood by those skilled in the art, it is preferable to use as low an amount of excess hydrogen peroxide as possible and still accomplish an efficient conversion.

Typically, the molar ratio of urea-hydrogen peroxide to olefin to MTO will be in the range from 1200:120:1 to 300:120:1, with the rhenium catalyst present at a level of 0.5–5.0 mole percent with respect to olefin. Preferably the ratio will be about 600:120:1, and more preferably will be about 300:120:1.

This process may be used to epoxidize any organic compound having at least one ethylenically unsaturated functional group (carbon-carbon double bond), and may be aromatic, aliphatic, mixed aromatic-aliphatic, cyclic, branched or straight chain. The process is especially useful for the epoxidation of olefins having 2 to 30 carbon atoms.

Suitable solvents for the reaction medium include tetrahydrofuran, monovalent aliphatic alcohols with 1–5 carbon atoms, and aromatic hydrocarbons, such as, toluene and xylene. The preferred solvent for the reaction is tertiary-butyl alcohol.

The following examples are given to illustrate the invention further, and should not be deemed as a limitation on the scope of the invention.

EXAMPLES

Example I

Syntheses of Epoxides.

A series of epoxides was prepared using urea-hydrogen peroxide as the oxidant in the presence of methyltrioxorhenium (MTO) catalyst according to the procedure:

To a 50 ml multinecked flask fitted with a reflux condenser, thermometer, and magnetic stirrer were charged 2.83 g (30 mmol) of urea-hydrogen peroxide (UHP), 15 ml of tert-butyl alcohol, and 25 mg of methyltrioxorhenium (MTO). The resulting slurry was allowed to stir for five minutes and then the olefin was added in the amount and in the mole ratio to the peroxide and catalyst as reported in Table I. The mixture was stirred at room temperature until the reaction was judged by gas chromotography to be complete, which is the time reported. The mixture was diluted with 25 ml of ethyl ether and then cooled in an ice bath. The urea was filtered off and the filtrate washed with two 25 ml portions of 5% sodium sulfite followed by one 25 ml portion of water. The organic layer was dried over magnesium sulfate and then concentrated in vacuo. The concentrate was purified by distillation under reduced pressure.

The results are tabulated in Table I. Yields are given as normalized area percents of components (olefin, epoxide, and diol) obtained by gas chromatography, and may be considered as weight ratios.

TABLE I

| Olefin | Cyclododecene | Cyclohexene | Trans 4,5-octene |
|---|---|---|---|
| Substrate | 4.15 g | 1.02 g | 1.40 g |
|  | 24.9 mmol | 12.4 mmol | 12.5 mmol |
| Reaction Time hours | 1 | 2 | 2 |
| Product | Cyclododecene oxide | Cyclohexane oxide | 4,5-epoxyoctane |
|  | 3.75 g | 1.10 g |  |
|  | 20.5 mmol | 11.3 mmol |  |
| Percent Yield | 82% (isolated) | 91% (isolated) | 88% (GC) |

Example II

Allylbenzene (AB) was epoxidized to 2,3-epoxypropylbenzene in a series of reactions according to the procedure of Example I with variations in the mole ratios of UHP:AB:MTO, reaction times and temperatures as reported here. The reaction conditions and percent yield (as a weight ratio of olefin, epoxide, and diol, using gas chromatography) are set out in Table II.

TABLE II

| Mole Ratio | | | Reaction Conditions | | Percent Yield | |
|---|---|---|---|---|---|---|
| UHP | AB | MTO | °C. | Hours | % Oxide | % Diol |
| 112 | 30 | 1 | 25 | 67.5 | 87.3 | 0.3 |
| 62 | 30 | 1 | 35 | 20 | 83.9 | 0.4 |
| 62 | 30 | 1 | 45 | 7 | 75.9 | 0.5 |
| 62 | 30 | 1 | 60 | 3.5 | 47.5 | 0.5 |

These results are to be compared to the epoxidation of allylbenzene using aqueous hydrogen peroxide, which gave lower selectivity to the epoxide, higher levels of diol formation, and longer reaction times. The mole ratio of reactants was the same as the first entry in Table II, namely, $H_2O_2$:AB:MTO::112:30:1. Water was initially removed by drying a mixture of t-butanol, α-methylbenzyl alcohol (α-MeBzOH), and 30% hydrogen peroxide ($H_2O_2$) over anhydrous magnesium sulfate, followed by removal of the hydrated salt by filtration. After titrimetric determination of both water content and active oxygen, the appropriate volume of solution was added to a multinecked flask, followed by the addition of MTO and allylbenzene. The reagents were admixed as described above, and after 43 hours at 25° C. the reaction yielded 46% of the epoxide and 7.4% of the diol by-product. A second reaction was conducted for four (4) hours at 45° C. and yielded 61% of the epoxide and 17% of the diol.

Example III

Using the procedure of Example I, allyl phenyl ether (APE) was epoxidized to phenyl glycidyl ether using a mole ratio of UHP:APE:MTO of 300:120:1, in a 46% conversion in two hours at 25° C., as determined by gas chromatography.

These results are to be compared to prior art epoxidations of APE using aqueous hydrogen peroxide and methyltrioxorhenium (MTO) catalyst in the presence of a secondary alkyl aryl alcohol. A mixture of t-butanol, α-methylbenzyl alcohol (α-MeBzOH), and 30% hydrogen peroxide ($H_2O_2$) were dried over anhydrous magnesium sulfate, followed by removal of the hydrated salt by filtration. After titrimetric determination of both water content and active oxygen, the appropriate volume of solution was added to a multinecked flask, followed by the addition of MTO and allyl phenyl ether. The reaction was stirred for eight hours. Although none of the diol, 3-phenoxy-1,2-propanediol, was detected in any of the reaction mixtures, the data show that the yields of epoxides were less than 10%. In addition, the experiments carried out in the presence of the α-methylbenzyl alcohol gave no improvement in yield over those in which it was absent. The mole ratios of $H_2O_2$:APE:MTO, the presence or absence of α-MeBzOH, the reaction temperature, and percent yield (as a weight ratio of olefin, epoxide, and diol, using gas chromotography) are reported in Table III.

TABLE III

| Comparative Data | | | | | | |
|---|---|---|---|---|---|---|
| Mole Ratio | | | Reaction Conditions | | | Percent Yield |
| $H_2O_2$ | APE | MTO | α-MeBzOH | °C. | Hours | % Oxide |
| 300 | 125 | 1 | yes | 25 | 8 | <1 |
| 300 | 125 | 1 | yes | 50 | 8 | 5.6 |
| 300 | 125 | 1 | yes | 60 | 8 | 5.1 |
| 300 | 120 | 1 | no | 25 | 8 | 7.6 |
| 200 | 85 | 1 | yes | 25 | 8 | 8.3 |
| 200 | 85 | 1 | no | 25 | 8 | 9.9 |

Example IV

Allylbenzene (AB) was epoxidized with hydrogen peroxide and the MTO catalyst in combination with 2,2-bipyridyl (BiPy) to test the effectiveness of bipyridyl to suppress diol formation in comparison with the use of urea-hydrogen peroxide. A mixture of t-butanol, 30% hydrogen peroxide ($H_2O_2$) and BiPy were dried over anhydrous magnesium sulfate, followed by removal of the hydrated salt by filtration. After titrimetric determination of both water content and active oxygen, the appropriate volume of solution was added to a multinecked flask, followed by the addition of MTO and allylbenzene. The mole ratio of $H_2O_2$:AB:MTO:BiPy, the reaction times and temperature, and percent yields of epoxide and diol (as a weight ratio of olefin, epoxide, and diol, using gas chromotography) are reported in Table IV.

TABLE IV

| Comparative Data | | | | | | | |
|---|---|---|---|---|---|---|---|
| Mole Ratio | | | | Reaction Conditions | | Percent Yield | |
| $H_2O_2$ | AB | MTO | BiPy | °C. | Hours | Oxide | Diol |
| 110 | 30 | 1 | 0 | 25 | 70 | 69.7 | 6.06 |
| 110 | 30 | 1 | 6 | 25 | 192 | 93.2 | 1.2 |
| 110 | 30 | 0.5 | 3 | 25 | 144 | 54.3 | 0.4 |
| 110 | 30 | 1 | 3 | 25 | 164 | 80.6 | 1.46 |
| 225 | 30 | 1 | 6 | 25 | 92 | 82.8 | 0.7 |
| 225 | 30 | 1 | 12 | 25 | 92 | 70.1 | 0.5 |
| 225 | 30 | 1 | 6 | 35 | 12 | 76.2 | 0.7 |
| 225 | 30 | 1 | 6 | 45 | 7 | 65.1 | 0.9 |
| 225 | 31 | 1 | 6 | 60 | 3.5 | 64.0 | 2.4 |

These data show that although bipyridyl is generally effective at suppressing diol formation, the concomitant modulation of catalyst activity also results in longer reaction times, higher temperatures, and greater amount of peroxide required to bring about the conversions to epoxide than are required using UHP. Using the results in Table II for comparison, it can be seen, for example, that the same reaction conditions of 45° C. and 7 hours gave a 65% yield of epoxide and a 0.9% yield of diol for the BiPy reaction compared to a 75.9% yield of epoxide and a 0.4% yield of diol using UHP. Moreover, the amount of peroxide needed for these results was considerably higher in the reaction in which bipyridyl was present.

As a further example, when the molar ratios are comparable, 110/112:30:1 (peroxide:olefin:MTO), the epoxide formation is slightly more favorable in the presence of the BiPY, but the reaction time is significantly longer (192 hours compared to 67.5 hours) and the diol formation is greater (1.2% compared to 0.3%).

These Examples demonstrate that urea-hydrogen peroxide, in combination with methyltrioxorhenium catalyst, gives an unexpected striking advantage in epoxidations in comparison to prior art methods, giving good conversions to epoxide and inhibiting diol formation.

We claim:

1. A process for the epoxidation of olefins comprising contacting the olefin with urea-hydrogen peroxide in the presence of a rhenium catalyst in an organic solvent.

2. The process according to claim 1 in which the rhenium catalyst is methyltrioxorhenium.

3. The process according to claim 1 in which the mole ratio of urea-hydrogen peroxide:olefin:rhenium catalyst is about 300:120:1.

* * * * *